US007970714B2

(12) United States Patent
Heiden

(10) Patent No.: US 7,970,714 B2
(45) Date of Patent: Jun. 28, 2011

(54) SYSTEM AND METHOD FOR PRODUCING A MAILPIECE INCLUDING VALUE ADDED SERVICES

(75) Inventor: Richard W Heiden, Shelton, CT (US)

(73) Assignee: Pitney Bowes Inc., Stamford, CT (US)

( * ) Notice: Subject to any disclaimer, the term of this patent is extended or adjusted under 35 U.S.C. 154(b) by 1486 days.

(21) Appl. No.: 11/187,408

(22) Filed: Jul. 22, 2005

(65) Prior Publication Data

US 2007/0022059 A1 Jan. 25, 2007

(51) Int. Cl.

| | |
|---|---|
| ***G06F 17/00*** | (2006.01) |
| ***G06F 9/00*** | (2006.01) |
| ***G07B 17/02*** | (2006.01) |
| ***B31B 1/88*** | (2006.01) |
| ***B65B 11/48*** | (2006.01) |
| ***B65B 11/00*** | (2006.01) |
| ***B65B 49/00*** | (2006.01) |
| ***A01H 5/00*** | (2006.01) |

(52) U.S. Cl. ........ 705/401; 705/408; 705/410; 493/187; 101/371; 53/460; 53/461

(58) Field of Classification Search .................. 705/401
See application file for complete search history.

(56) References Cited

U.S. PATENT DOCUMENTS 6,456,987 B1 * 9/2002 Pauschinger .................. 705/408
6,532,452 B1 * 3/2003 Pintsov et al. ................ 705/401
2002/0023057 A1 * 2/2002 Goodwin et al. ............... 705/50
2005/0111047 A1 * 5/2005 Rhoads ........................ 358/3.28

OTHER PUBLICATIONS

Insurance E-Businesses Find Niches; Savvy Companines like InsurePoint.com and CertificatesNow.com Fill Industry Gaps. Hoffman, Thomas: Computerworld, Jan. 31, 2000, p. 42. from Dialog.*

* cited by examiner

*Primary Examiner* — John W Hayes
*Assistant Examiner* — David J Clark
(74) *Attorney, Agent, or Firm* — Brian A. Collins; Charles R. Malandra, Jr.; Steven J. Shapiro

(57) ABSTRACT

A system for producing a mailpiece for delivery in accordance with a Value Added (VA) service. The system comprises a computer processor having Value Added Services (VAS) program code adapted to operate in combination with the processor's print driver code. Further, the VAS program code is operative to receive operator input data in connection with a Value Added Service. Additionally, the system includes at least one peripheral device, operating in combination with the VAS program code, for (i) determining charges in connection with the mailpiece based upon the VA service and (ii) printing VAS data/postage indicia on the mailpiece. In one embodiment of the invention, the system includes a VAS database for collecting VAS data and performing various accounting services (e.g., charge-back, financial tracking) or producing a manifest document when using a Manifest Mailing System. The method includes the steps of attaching the VAS program code to the print driver code and/or registering the VAS code with the peripheral device to establish the location or portal for sending integrated VAS data.

16 Claims, 6 Drawing Sheets

70

| | | | | | | | | | |
|---|---|---|---|---|---|---|---|---|---|
| **MANIFEST DOCUMENT** | | **Date of Manifest:** 03/04/05<br>**Office of Mailing:** Shelton PO | | | | | | **Number of Pages:** 1 | |
| **Mailers Name:** Pitney Bowes<br>**Address:** | | **Permit Number:** 09223775<br>**Processing Category:** Mixed | | | | | | | |
| **Mailpiece ID Number** | **Confirmation – Article Number** | **Zip Code** | **Weight** | **Class/ Rate** | **Postage** | **Insured Value** | **Fee** | **Total Charges** | Cumulative Charges |
| 1298 | 0004488994774 | 45235 | 2.25 | PF | 3.85 | | | 3.85 | 3.85 |
| 1395 | 2288574999886 | 10710 | 25.87 | 1P | 26.60 | 100.00 | 3.40 | 30.00 | 33.85 |
| 1492 | 0000394857756 | 06610 | 24.12 | IM | 7.24 | | | 7.24 | 41.09 |
| 1589 | 5566387964753 | 06610 | 0.12 | 1 | 1.06 | | | 1.06 | 42.15 |
| 1677 | 3334456785632 | 10710 | 0.54 | 1 | 2.21 | | | 2.21 | 44.36 |
| 1783 | 2345719864753 | 44467 | 12.25 | BN | 19.24 | 200.00 | 7.46 | 26.70 | 71.06 |
| 1880 | 2224354547858 | 99548 | 10.02 | BN | 16.65 | | | 16.65 | 87.71 |
| 1977 | 3779009766586 | 59074 | 15.21 | IN | 7.85 | | | 7.85 | 95.56 |
| 2074 | 5000897535790 | 63354 | 3.25 | 1P | 3.35 | | | 3.35 | 98.91 |
| 2171 | 4678644785378 | 63354 | 3.25 | BRX | 6.04 | | | 6.04 | 104.95 |
| 2268 | 3435754325678 | 06610 | 0.54 | BR | 2.31 | | | 2.31 | 107.26 |
| 2365 | 3000876443675 | 10710 | 0.12 | 1 | 1.06 | | | 1.06 | 108.32 |
| 2559 | 3546765478643 | 46803 | 10.55 | 1PX | 20.55 | 300.00 | 14.07 | 34.63 | 142.95 |
| 2655 | 3345378866898 | 46846 | 12.21 | IM | 6.65 | | | 6.65 | 149.60 |

FIG. 5

SYSTEM AND METHOD FOR PRODUCING A MAILPIECE INCLUDING VALUE ADDED SERVICES

FIELD OF THE INVENTION

The present invention relates to a system and method for producing a mailpiece, and more particularly, to a system and method for producing mailpieces having a Value Added Service (VAS).

BACKGROUND OF THE INVENTION

The vast majority of mailpieces for delivery by a mail carrier enter the mail distribution system via a mailbox, kiosk, or similar device. One of the few instances that a visit to a local post office or carrier service may be required relates to certain requests for special handling or delivery of a mailpiece, i.e., requests for Value Added (VA) services. That is, should it be decided that "First Class" or "Priority" mailing is required to expedite delivery, a trip to the post office may then be required. Processing the request typically involves the completion of one or more forms, a review of the completed form(s) by a mail clerk, calculation of the required postage and induction of the mailpiece into the mail delivery system. As such, it will be appreciated that this manual process is laborious, time consuming and costly.

Difficulties associated with obtaining VA services is exacerbated in those instances where multiple mailpieces are to be delivered, e.g., bulk mailing of an advertisement to a large number of recipients. Rather than individually weighing and/or applying postage to each mailpiece, the United States Postal Service (USPS) encourages the use of a Manifest Mailing System (MMS) which is an automated postage payment system used to calculate and document postage. While a manifest is any listing of multiple mailpieces, in the context of the MMS, a manifest is a document which includes (i) a sequential listing of mailpieces in a batch or tray, (ii) a calculation of the postage based upon various rate options and presort levels claimed, and (iii) a signed/executed statement that, to the best of the mailer's belief, the calculated postage is true and correct.

Qualification to use the MMS requires that a mailer meet certain minimum requirements, i.e., 200 mailpieces or 50 pounds which may be satisfied by the mailing of mixed classes in the same batch. That is, to the extent that a mailer does not have the minimum 200 mailpieces in a particular class, the MMS permits a batch to include any one of a variety of classes, e.g., First Class, Certified, Return Receipt etc. Consequently, an itemized manifest, i.e., listing each mailpiece together with its class of service, may be used wherein, upon induction, a mail clerk accepts the batch, samples a few mailpieces (e.g., weighting each of the few selected) and approves the manifest. Of course, the USPS reserves the right to audit any of the manifests submitted for delivery.

The MMS significantly reduces the time sorting, labeling and calculating postage for the USPS, however, the burden is merely shifted to the mailer (albeit discounts are available as an incentive to use the MMS). While certain sophisticated mailers, who routinely prepare bulk mailings, may take full advantage of the MMS, many others lack the necessary proficiency (i.e., inefficient in the practice of printing, presorting and generating a manifest) to use the system effectively. This is particularly true for mailers requiring a variety of VA Services (i.e., mixed classes of mail) for mailing its products or services as part of its daily business. To request such VA services, specialized labels are typically required inasmuch as postage requirements vary from one class of mail to another.

With respect to the foregoing, an automated approach to printing labels, envelopes and manifest documents via a computerized system could provide significant efficiencies. On the other hand, the investment of time and funds may be difficult to justify when employing conventional tools and/or techniques for its development/implementation. More specifically, when modeling a solution based upon traditional software architecture, one of two development paths is commonly considered. These include creating dedicated application software or, alternatively, introducing specialized program code for each application. With respect to dedicated software, this approach requires that, each time a VA service may be requested, the user (i) leave a current software application e.g., word processing software, (ii) launch the dedicated VA service software and (iii) input data which may already exist in the other software application, i.e., where the mailpiece may have originally been created. Aside from the inconvenience of opening dedicated VA service software, such software requires additional data input for preparing each mailpiece. With respect to the development of specialized program code, each of the software applications (i.e., hundreds of applications which may be capable of producing mailpieces requiring VA services) would now require individual program modification.

In view of the absence of such software in the marketplace, whether dedicated application software or as a modification to existing application software, it may be reasonable to conclude that there is insufficient demand for this type of software product/product modification.

A need, therefore, exists to facilitate the creation of mailpieces having a VA service, minimize data input associated with mailpiece production, and mitigate complexities associated with the MMS while expediting the preparation of a manifest document.

SUMMARY OF THE INVENTION

A system is provided for producing a mailpiece for delivery in accordance with a Value Added (VA) service. The system comprises a computer processor having Value Added Services (VAS) program code adapted to operate in combination with the processor's print driver code. Further, the VAS program code is operative to receive operator input data in connection with a Value Added Service. Additionally, the system includes at least one peripheral device, operating in combination with the VAS program code, for (i) determining charges in connection with the mailpiece based upon the VA service and (ii) printing VAS data/postage indicia on the mailpiece. In one embodiment of the invention, the system includes a VAS database for collecting VAS data and performing various accounting services (e.g., charge-back, financial tracking) or producing a manifest document when using a Manifest Mailing System.

The method includes the steps of attaching the VAS program code to the print driver code and/or registering the VAS code with the peripheral device to establish the location or portal for sending integrated VAS data.

BRIEF DESCRIPTION OF THE DRAWINGS

Reference is now made to the various figures wherein like reference numerals designate similar items in the various figures and in which:

FIG. 5 depicts an exemplary manifest document produced by the method of the present invention.

DETAILED DESCRIPTION OF THE PREFERRED EMBODIMENT

A system and method is described for producing a mailpiece in combination with a Value Added (VA) service and/or including Value Added Services (VAS) data. In the context used herein, a VA service may include a request for expedited delivery of a mailpiece (e.g., overnight delivery), a signed acknowledgement that the recipient has received the mailpiece (e.g., return receipt), or a system for tracking the expenses/charges incurred by a particular customer or group of customers (e.g., a charge-back accounting system) Moreover, the system and method are described in the context of computer architecture having a standard operating system which employs program code for accessing at least one print driver. An exemplary operating system which may be adapted to employ the teachings of the invention includes Windows® 2000 OS (Windows is a registered trademark of Microsoft Corporation having its principle operations in the State of Washington, USA). It should be appreciated, however, that the invention may be adapted to any operating system which provides access to and/or modification of its print driver program code.

The invention also describes program code adapted to operate a computer, display a dialog box, and/or effect certain printing options. To the extent that one skilled in the art can readily produce program code to (i) cause a computer to perform conventional operations, (ii) display a user interface for interaction with a keyboard or "point-and-click" input device such as a computer mouse, or (iii) provide communication protocol between commonly connected devices, e.g., a printer and a mailing machine, such program code will only be described as method steps or in algorithmic form. It will be appreciated that program code of the type described can be produced in many computer languages and arranged in a variety of ways. Consequently, such program code will not be described in greater detail and only to the extent that one skilled in the art can, with the teachings of the invention, construct suitable program code to perform the functions described herein.

In the broadest sense of the invention, the system for producing a mailpiece including a Value Added (VA) service comprises: a computer processor having Value Added Services (VAS) program code adapted to operate in combination with the processor's print driver code. Further, the system includes at least one peripheral device, operating in combination with the VAS program code, for (i) determining charges in connection with the mailpiece and (ii) printing VAS data/postage indicia on the mailpiece. In one embodiment of the invention, the system includes a data storage means for collecting VAS data, and performing various accounting services (e.g., charge-back, financial tracking) or producing a manifest document.

Figure 1A:
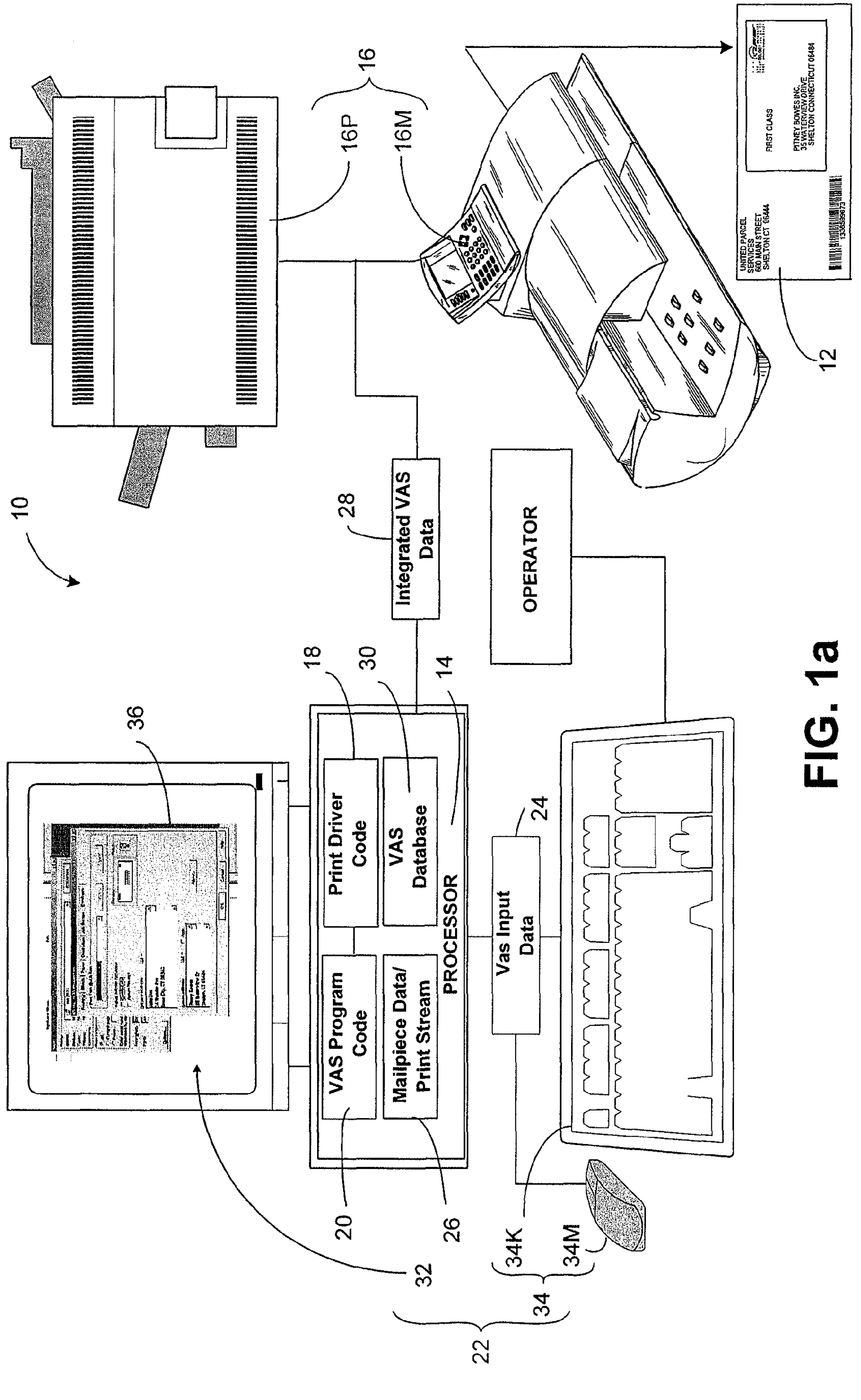
FIGS. 1*a* and 1*b* are schematic block diagrams of a system for producing a mailpiece for delivery pursuant to a Value Added (VA) service including VAS program code disposed in combination with print driver code of a computer processor, and a peripheral device for producing/printing a mailpiece, mailpiece envelope, and/or mail manifest document.
Figure 1B:
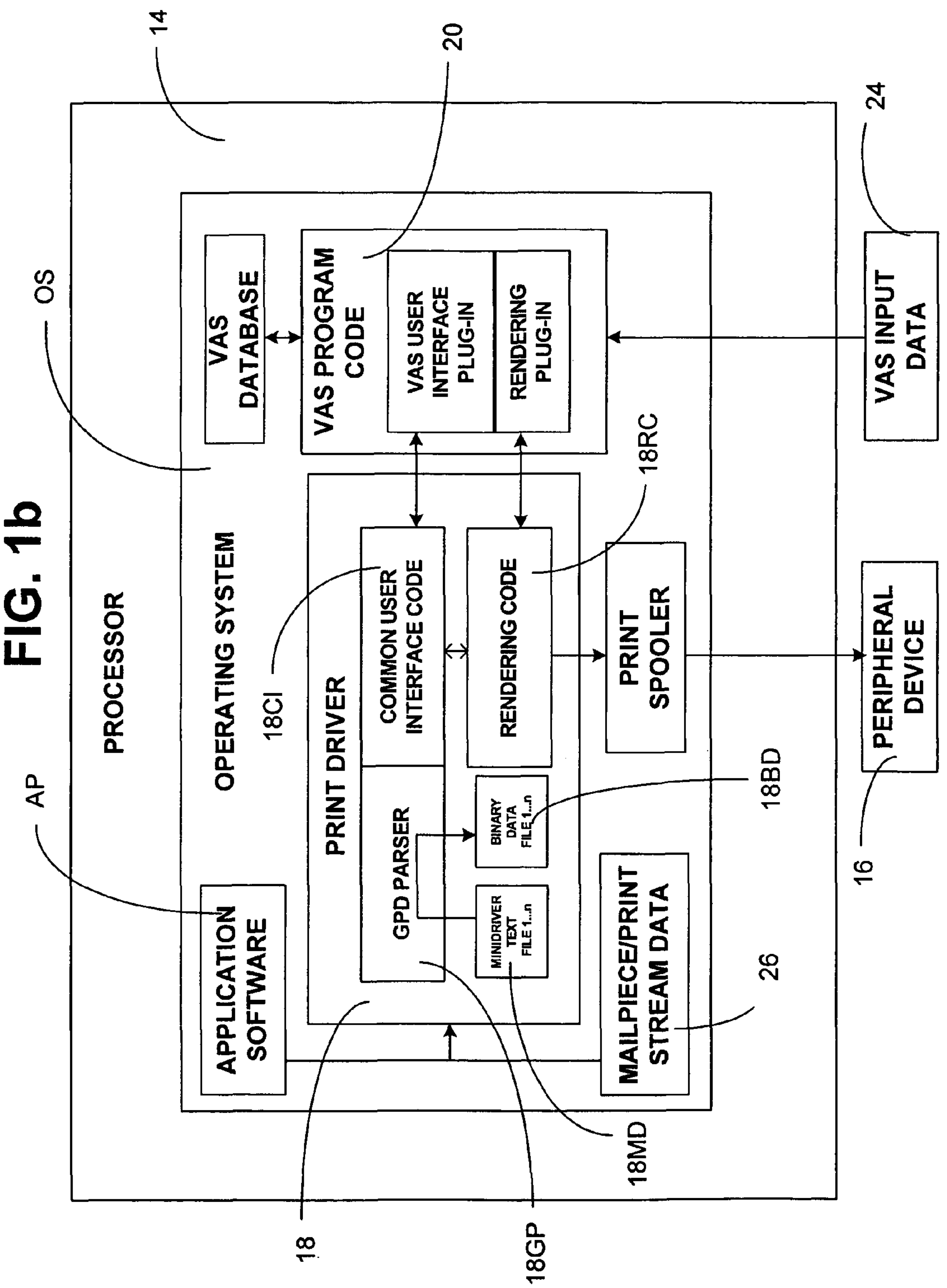

More specifically, and referring to FIGS. 1*a* and 1*b*, the system 10 for producing a mailpiece 12 comprises a computer or computer processor 14 (these terms being used interchangeably), and at least one peripheral device 16 such as a printer 16P and/or mailing machine 16M (seen in FIG. 1*a*). While only a printer 16P and mailing machine 16M are illustrated, it will be appreciated that other peripheral devices including inserters, folders and/or weighing devices may be employed for mailpiece creation. The computer processor 14 includes an operating system OS for conducting and controlling various kernel space processes and various application software AP, or user space processes, for performing specific tasks or operations such as word processing, spreadsheet calculations, or graphics production.

In FIGS. 1*a* and 1*b*, the operating system OS includes print driver program code 18 operable to provide the communication protocol, or to translate the print commands of various application software AP into a protocol, understandable by the printer 16P. Such print driver program code 18 is commonly employed in personal computers in view of the myriad of printers which must operate seamlessly with the various application software AP installed on the computer 14. The print driver program code 18 includes common user code 181C, i.e., code which selects/controls the various functions and properties of the numerous printers supported by the operating system OS. As such, the print driver code 18 is commonly referred to as "universal" or "generic" print driver code 18 inasmuch as the code 18 controls the vast array of common printer characteristics and functions. The print driver code 18 also includes rendering code 18RC which controls various graphics features available or supported by the operating system OS. The rendering code 18RC provides the print driver code 18 with the ability to produce certain graphics or symbols, e.g., print a barcode symbol. Moreover, the print driver code 18 includes a GPD Parser 18GP which functions to convert the text file description 18MD of the common user code 181C into a more useable binary data file format 18BD.

In the described embodiment, the common interface and rendering codes 181C, 18RC are capable of accepting "plug ins" or other program code for modifying the print driver code 18. While the type of modifications typically anticipated are those required for specialty printing or unique printers, the present invention uses this resource or plug-in capability to introduce Value Added Services (VAS) program code 20.

The VAS program code 20 is operative to: (a) provide an electronic interface 22 for receiving VAS input data 24 in connection with a Value Added (VA) service (i.e., data input by an operator regarding a Value Added service), (b) integrate the VAS input data 24 with other mailpiece/print stream data 26 to produce integrated VAS data 28, and (c) create/maintain a VAS database 30 relating to the VA services, i.e., storing/tracking data relating to the mailpiece 12 and the VA service associated therewith. With respect to the latter, the VAS database may be used for (i) determining charges in connection with delivery of the mailpiece 12, (ii) printing the integrated VAS data 28 to produce the mailpiece 12 and (iii) developing a manifest document when using the Manifest Mailing System (MMS).

The printer and mailing machine 16P and 16M are conventional, however, the VAS program code, discussed in greater detail in subsequent paragraphs, controls these devices in an unconventional manner. Before discussing the VAS program code 20 in greater detail, however, it is useful to briefly describe the remaining elements of the system architecture.

The printer 16P may be any of a variety of devices including dot-matrix, inkjet, bubble jet, or laser printers. Generally, any printer capable of printing envelopes or labels may be employed. In the described embodiment, a primary purpose of the printer 16P is the generation of mailpiece content, however, another use (described in greater detail below when discussing the system function) may include printing a machine and/or human readable symbol for mailpiece identification. The mailing machine 16M may be for example, one of the DM series mailing machines designed and manufactured by Pitney Bowes Inc. having it base operations in Stamford, Conn. While this mailing machine 16M has many features and functions which are useful for creating mailpieces, the functions relating to weighing and printing human/machine readable postage/postage indicia are relied upon for practicing the present invention.

Figure 2:
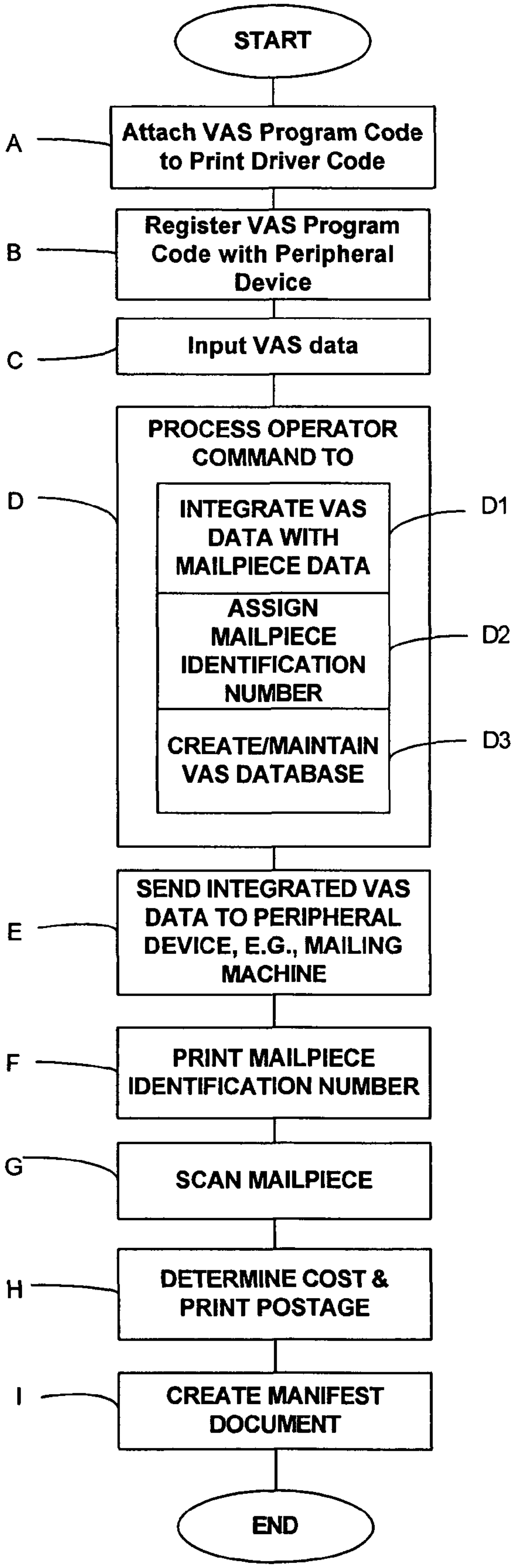
FIG. 2 is a flow diagram of the method steps employed for set up and operation of the VAS program code in combination with the peripheral device, e.g., a mailing machine.
Figure 3:
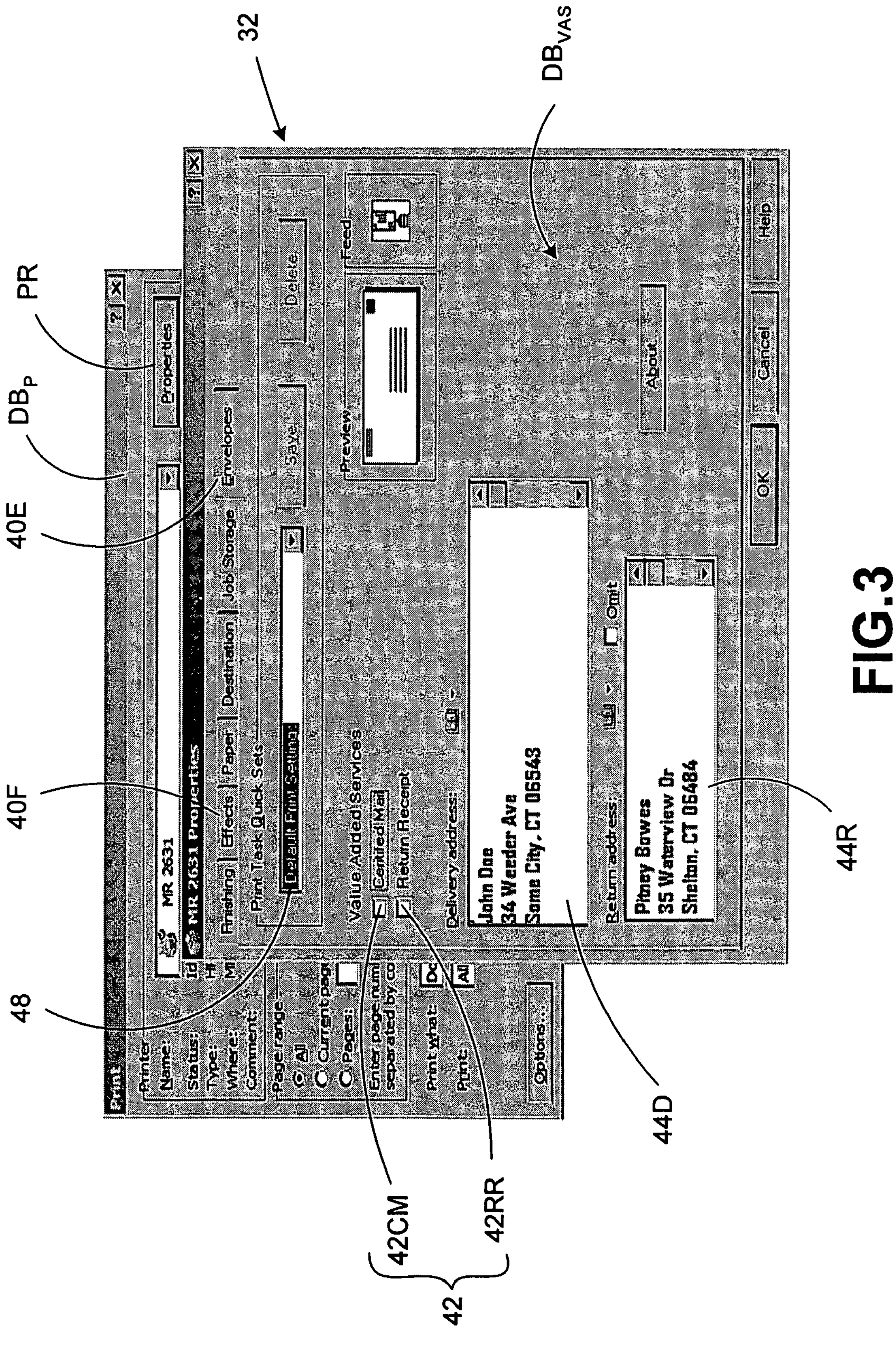
FIG. 3 illustrates a dialog box generated by the VAS program code for integrating operator input data with other mailpiece data, i.e., the mailpiece print stream.

FIG. 2 depicts a flow diagram of the set-up and operation of the inventive system 10. In step A, the VAS program code 20 is attached to the print driver program code 18. In the context used herein "attached" is an action performed in computer software which causes new program code to be added and run with existing program code. In step A, therefore, the VAS program code 20 is added to and runs with the common user interface and rendering codes 18CI, 18RC of the print driver code 18. The attached VAS program code 20 does not alter the functionality of the print driver code 18, but rather is a "plug-in" or "intercept" which augments the functionality of the print driver code 18. In step B, the VAS program code 20 also registers with the peripheral device 16, e.g., the mailing machine 16M, which is networked with the processor 14. By "registering" is meant that that the VAS code 20 identifies itself to the peripheral device 16, i.e., the mailing machine 16M which, in turn, allows the peripheral device 16 to identify mailpieces having VAS data. The underlying program code to effect attachment and registration of one software product to another are well-understood to those skilled in the art and, to facilitate the description, will not be discussed further herein. Suffice it to say that attachment/registration is capable of being accomplished by one possessing ordinary skill in the art based upon the teachings provided herein.

Referring to FIGS. 1*a*-3, to produce a mailpiece 12 having a Value Added service, information in connection with the basic print commands is provided by the universal print driver 18. A conventional dialog box $DB_P$ in connection with the universal print driver 18 is produced/displayed and may include information such as the type of printer, printer status, portal for printing, print range, number of copies, collation requirements etc. Included therein is an electronic link to access the VAS program code 20 for providing the VAS input data 24. The electronic link may be a simple computer generated call button such as the "properties" button PR typically appearing in conjunction with the print driver dialog box.

More specifically, in step C, VAS program code 20 provides a Graphic User Interface (GUI) 32 for accepting the VAS input data 24 from an input device 34 such as a keyboard 34K or computer mouse 34M. The GUI 32 may present a conventional dialog box $DB_{VAS}$ (see FIG. 3) for displaying various icons, check boxes, selection buttons or flags to the operator regarding printing options and VA services requested. For example, the operator may elect to print on an envelope by selecting an envelope flag 40E or, alternatively, on create special effects selecting the effects flag 40F. A particular VAS service may be selected by various check boxes 42. Only two such checkboxes are depicted, i.e., a checkbox 42CM for "certified mail" and another checkbox 42RR for "return receipt", however, the number of such selection boxes may correspond to the number of VAS services offered by postal services or mail carriers. For example, additional checkboxes can be provided for insurance coverage, registered mail, Cash-On-Delivery (COD), Special Handling, Parcel Airlift, etc.

Inasmuch as the VAS input data 24 will be integrated with other mailpiece data 26, i.e., data in the print stream, the dialog box $DB_{VAS}$ may display portions of such data to preview the information or print format thereof. For example, a destination address window 44D and return address window 44R may be provided to review select mailpiece data in advance of printing. Yet other drop-down or selection buttons 48 may be provided including whether to use the standard default print settings when printing on an envelope or label. The dialog box $DB_{VAS}$ as illustrated is not intended to display an exhaustive list of possible selection options, but merely shows how an electronic interface 22 may be constructed in the context of the present invention.

Following entry of the input data, in step D, the VAS data 24 is processed in combination with other mailpiece data 26 to produce integrated VAS data 28. More specifically, in step D1, the VAS program code 20 integrates the VAS data 24 with the mailpiece print stream 26 and, in step D2, generates data elements which uniquely identify the mailpiece, e.g., assigns a unique numeric code to the mailpiece, and information in connection with the type of VA service requested. Alternatively, the mailing machine 16M, in communication with the processor 14, may assign the unique identifier to the mailpiece 12. In step D3, the VAS program code 20 records and/or stores these data elements in a VAS database 30 residing in the processor memory. At minimum, the VAS database 30 will store the assigned mailpiece identification number and information relating to the type of VA service being requested. For example, the database 30 may retain and receive updates concerning the current charges for such VA services by particular postal service providers. Furthermore, as will be discussed in subsequent paragraphs, the database 30 may be used in connection with generating a manifest document when using the Manifest Mailing System (MMS).

In step E, the integrated VAS data 28 is then sent to a destination address, established in the registration step B discussed above, corresponding to the location or portal of the peripheral device 16. Generally, the VAS data 28 will be routed to a dedicated mailing machine 16M, however, if the mailpieces 12 are generated by one of a plurality of senders, i.e., each having a dedicated mailing machine 16M, then the integrated VAS data 28 may be directed to a portal/mailing machine 16M corresponding to the particular sender.

Figure 4:
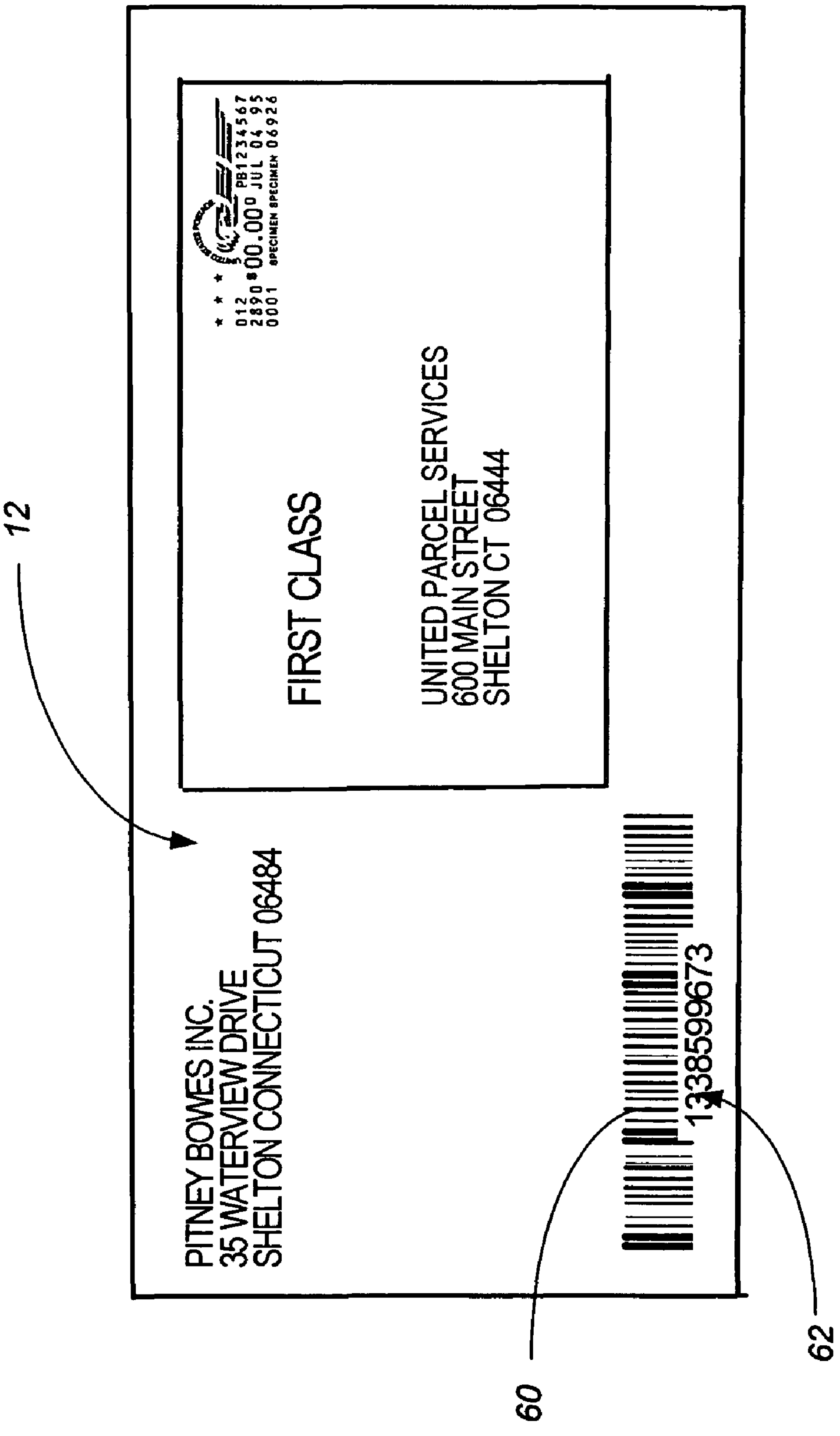
FIG. 4 is a mailpiece produced by the system including machine and human readable VAS data for use by the peripheral device or a postal carrier/agent upon delivery of the mailpiece.

In step F, the printer 16P prints the mailpiece content material and mailpiece envelope. More specifically, the mailpiece identification number and any special markings which may be desirable or required in connection with the VAS service are printed on the envelope 12. Referring additionally to FIG. 4, the printer 16P may print a machine readable symbol, for example, a barcode symbol 60 indicative of the mailpiece identification number 62, on the face of the mailpiece 12. In a subsequent step G, a mailing machine 16M equipped with a general purpose scanner (not shown) reads the barcode symbol 60 such that the mailpiece identification number 62 can be cross-referenced with the VAS database 30. In this way, the fixed expenses or charges associated with the VA services requested may be obtained. Furthermore, with the content material disposed within the mailpiece envelope, the mailpiece 12 is weighed to determine the cost based upon weight. The variable expense associated with mailpiece weight may then be combined with the fixed expense associated with a VA service (stored in the VAS database 30 of the processor 14) to obtain the total cost for delivery of the mailpiece 12.

This calculation may be performed by either the computer processor 14 or a mailing machine 16M equipped with a general purpose processor (not shown). To the extent, however, that the variable expense of the mailpiece weight is obtained by the mailing machine 16M, it may be preferable to acquire the fixed expense of the VA service by communicating with the VAS database 30 over a network and calculate the total cost by the mailing machine 16M. Notwithstanding where the calculation is performed, the mailing machine 16M prints the postage indicia indicative of the total cost on the mailpiece 12.

In addition to calculating the required postage, the processor 14 may. In step H perform accounting services such as tracking, storing and/or assigning charges to various customers/client accounts. For example, the portal for the mailing machine may be associated with a particular customer/client such that all mailpieces created at that address, i.e., on that mailing machine, will be recorded and charged back to the customer/client.

In addition to printing the mailpiece, a manifest document 70, a sample thereof being illustrated in FIG. 5, may be produced by the system 10 in step 1. Inasmuch as the database 30 records and stores information relative to the VA services, and the peripheral device, in combination with the processor 14, cooperate to determine postage for each mailpiece 12, the system may be adapted to produce a manifest document 70 in the format desired by a postal agent or mail service provider. To the extent that the manifest requires information pertaining to mailpiece identification (Column II), the VA service (Column IV), mailpiece weight (Column V) and postage (Column VI), the system 10 is uniquely suited to gather this information from the VAS database 30. Further, information pertaining to such items as the destination ZIP code (Column III), customer address (Column II) or insured value (Column VII) are available from the other mailpiece data/print stream or can be captured by the VAS program code from the input data, e.g., a checkbox for insured value. In addition to these elements, existing or acquired, the system need only generate a sequential listing of mailpieces (Column I) and perform elementary spreadsheet calculations (Columns VIII and IX) to complete the manifest document 70. Once again, the programming associated with organizing data in the format of the manifest document 70 will not be described herein inasmuch as such data manipulation can be readily performed by a skilled artisan.

In summary, the system and method produces a mailpiece having the requisite elements and data for delivery pursuant to a request for Value Added services. Furthermore, this capability is provided without the need for a dedicated (stand alone) software product or modification to existing software products used for mailpiece creation. That is, the drawbacks associated with these potential solutions are obviated by attaching the VAS program code 20 to the print driver code 18 residing in a computer system's operating system OS. Moreover, the system employs the existing or concurrently developed mailpiece data, i.e., the data print stream, without the need for redundant data entry. That is, having previously input, for example, a destination or return address into a software application, e.g., word processing software, the system 10 integrates the VAS input data without the need to re-enter or import data already existing (typically required when using dedicated software). Finally, the system and method facilitates financial tracking/accounting, e.g., charge-back allocation, postage calculations etc., and enables the production of supplemental documents such as a manifest.

While the present invention has been described in connection with what is presently considered to be the most practical and preferred embodiments, it is to be understood that the invention is not limited to the disclosed embodiment. For example, while the peripheral device 16 is illustrated as two separate electronic devices, i.e., a printer 16P and mailing machine 16M, it will be appreciated that the mailpiece printing (i.e., the contents of the mailpiece), weighing and printing postage may be performed by a peripheral device including a printing, weighing and metering station combined as an integral unit. Furthermore, while the processor 14 is shown in combination with a computer monitor and input device, i.e., a Personal Computer (PC) it will be understood that the processor 14 may be a single microprocessor located in a central processing unit or multiple processors cooperating together. That is, microprocessors may be disposed in a PC, a printer, and a mailing machine and communicate over a local or wide area network. It should be appreciated, therefore, that the system and method described herein is intended to cover various modifications and equivalent arrangements included within the spirit and scope of the appended claims.

What is claimed is:

1. A system for producing a mailpiece having a Value Added (VA) service and based upon operator provided Value Added Services (VAS) input data, the system comprising:

a processor having print driver code and Value Added Services (VAS) program code attached to the print driver code, the VAS program code operative to receive the VAS input data indicative of a Value Added (VA) service, and at least one peripheral device, operating in combination with the VAS program code, for printing the VAS data to produce the mailpiece.

2. The system according to claim 1 wherein the VAS program code is operative to provide an electronic graphical user interface for receiving the VAS input data.

3. The system according to claim 1 wherein the VAS program code is operative to integrate the operator input data with other mailpiece data to produce integrated VAS data for use by the peripheral device for printing the mailpiece.

4. The system according to claim 1 wherein the VAS program code is operative to create a VAS database for recording information in connection with the VA service and wherein the peripheral device determines mailpiece charges based on the information contained in the VAS database.

5. The system according to claim 1 wherein the VAS program code generates a data element which uniquely identifies the mailpiece, and wherein the peripheral device is adapted to read the data element for printing the VAS data on the mailpiece.

6. The system according to claim 1 wherein the at least one peripheral device includes one of a printer and a mailing machine.

7. The system according to claim 1 wherein the at least one peripheral device includes first and second peripheral devices and wherein the first peripheral device is a printer and the second peripheral device is a mailing machine.

8. The system according to claim 4 wherein the peripheral device, in combination with the processor, produce a manifest document based upon the VAS database.

9. A method for producing a mailpiece having a Value Added (VA) service and based upon operator provided Value Added Services (VAS) input data, the method comprising the steps of:

providing VAS program code operative to receive VAS input data in connection with a Value Added (VA) service, attaching the VAS program code to a print driver program code residing in a computer processor;

providing, using the VAS program code, an electronic interface to accept the VAS input data;

integrating, using the VAS program code, the operator input data with other mailpiece data to produce integrated VAS data;

directing, using the VAS program code, the integrated VAS data to at least one peripheral device;

printing the integrated VAS data to produce the mailpiece.

10. The method according to claim 9 wherein the step of providing an electronic interface includes the step of providing a graphical user interface for accepting the VAS input data.

11. The method according to claim 9 further comprising the steps of recording information in connection with the VA service in a VAS database and determining mailpiece charges based upon information contained in the VAS database.

12. The method according to claim 9 further comprising the steps of assigning a mailpiece identification number to the mailpiece and printing a machine readable symbol on the mailpiece indicative of the mailpiece identification number, the machine readable symbol being read by the peripheral device for cross-referencing the mailpiece identification number with information contained in the VAS database.

13. The method according to claim 9 wherein the step of directing the integrated VAS data includes the step of registering the VAS program code with the peripheral device.

14. The method according to claim 9 wherein the peripheral device includes one of a printer and a mailing machine.

15. The method according to claim 11 further comprising the step of producing a manifest document based upon the integrated VAS data and information contained in the VAS database.

16. The system according to claim 7 wherein the VAS program code generates data elements associated with identification of the mailpiece and the Value Added service, wherein the printer prints a symbol on the face of the mailpiece indicative of the data elements, and wherein the mailing machine, in combination with the processor, prints postage indicia on the mailpiece.

* * * * *